United States Patent
McDonald

(10) Patent No.: US 10,335,276 B2
(45) Date of Patent: Jul. 2, 2019

(54) TAVR VENTRICULAR CATHETER

(71) Applicant: Michael B. McDonald, Cordova, TN (US)

(72) Inventor: Michael B. McDonald, Cordova, TN (US)

( * ) Notice: Subject to any disclaimer, the term of this patent is extended or adjusted under 35 U.S.C. 154(b) by 446 days.

(21) Appl. No.: 15/288,525

(22) Filed: Oct. 7, 2016

(65) Prior Publication Data

US 2017/0020668 A1 Jan. 26, 2017

Related U.S. Application Data

(63) Continuation of application No. 14/097,524, filed on Dec. 5, 2013.

(60) Provisional application No. 61/733,818, filed on Dec. 5, 2012.

(51) Int. Cl.
*A61F 2/24* (2006.01)
*A61B 5/107* (2006.01)
*A61M 25/00* (2006.01)

(52) U.S. Cl.
CPC .......... *A61F 2/2427* (2013.01); *A61B 5/1076* (2013.01); *A61F 2/2496* (2013.01); *A61F 2230/0091* (2013.01); *A61F 2250/0098* (2013.01); *A61M 25/0041* (2013.01)

(58) Field of Classification Search
CPC .......... A61M 25/0041; A61M 25/0152; A61M 25/0662; A61M 2025/0161; A61F 2/2427; A61F 2/2436; A61F 2/2439; A61F 2/2442; A61F 2/2466
See application file for complete search history.

(56) References Cited

U.S. PATENT DOCUMENTS

| 4,738,667 A | * | 4/1988 | Galloway | A61M 25/04 604/530 |
|---|---|---|---|---|
| 2010/0014629 A1 | * | 1/2010 | Boese | A61B 6/4441 378/8 |
| 2010/0185172 A1 | * | 7/2010 | Fabro | A61B 1/00078 604/500 |
| 2014/0005540 A1 | * | 1/2014 | Merhi | A61F 2/013 600/435 |

* cited by examiner

*Primary Examiner* — Eric J Rosen
*Assistant Examiner* — Mikail A Mannan
(74) *Attorney, Agent, or Firm* — Angela Holt; Bradley Arant Boult Cummings LLP

(57) ABSTRACT

A catheter for positioning a valve during a transcatheter aortic valve replacement is formed from a resilient hollow body conformable to a guide wire when a guide wire is passed in through an upper opening in the hollow body and through the hollow body. When the guide wire is retracted, the catheter deploys to form a substantially straight upper shaft portion that extends downwardly from the upper opening and a distal ring perpendicular to the upper shaft portion. The distal ring approximates the size and shape of the patient's aortic valve annulus. An outer surface of the distal ring is radiopaque, and the distal ring comprises openings for dispersing radio opaque medium used in imaging. The deployed catheter is retracted until it snugly contacts the aortic valve annulus. The distal ring will be viewed as a straight line when the x-ray C-arm is properly aligned with the aortic valve annulus.

15 Claims, 5 Drawing Sheets

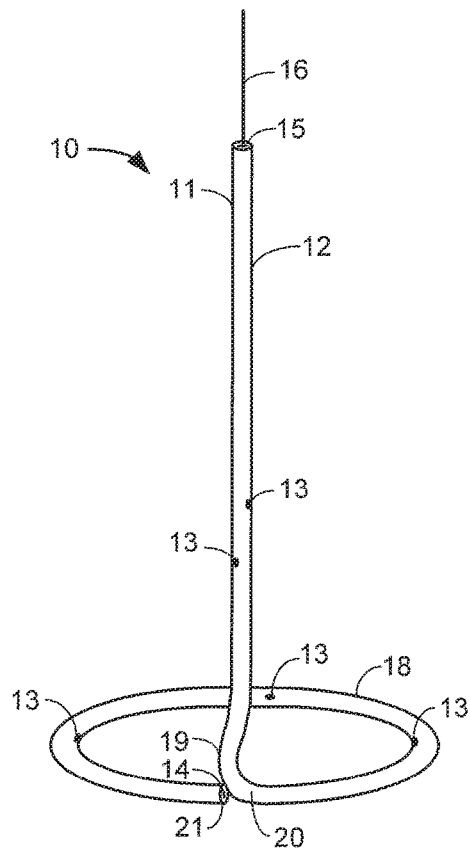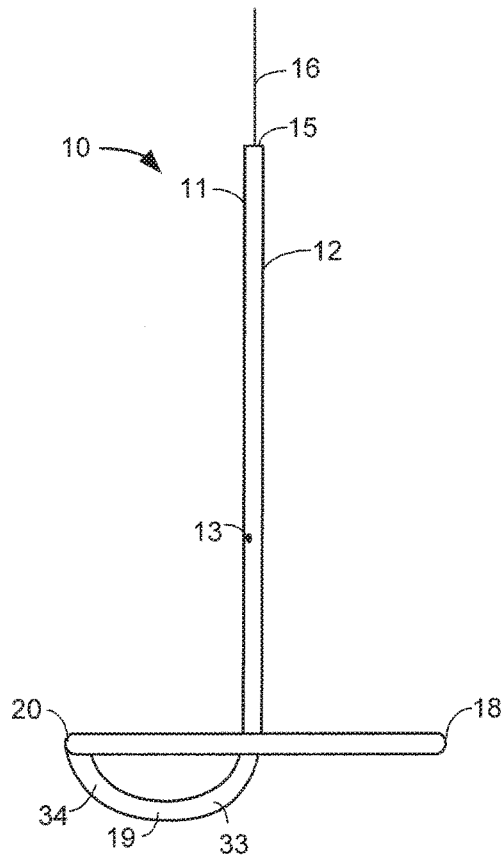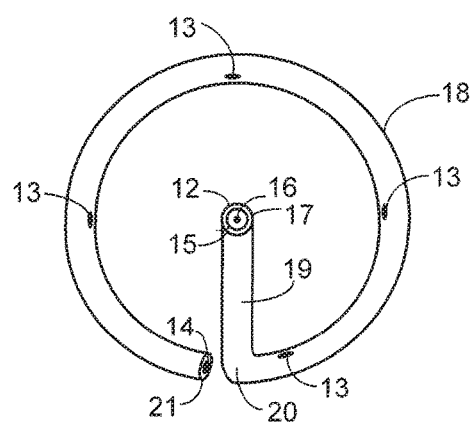

TAVR VENTRICULAR CATHETER

CROSS REFERENCE TO RELATED APPLICATIONS

This application is a continuation of U.S. application Ser. No. 14/097,524, filed on Dec. 5, 2013, which claims the benefit of and priority to U.S. Provisional Application Ser. No. 61/733,818, titled "TAVR Ventricular Catheter," filed on Dec. 5, 2012, the entire contents of both of which are herein incorporated by reference.

BACKGROUND AND SUMMARY OF THE INVENTION

Transcatheter aortic valve replacement (TAVR) is a treatment for stenosis of the aortic valve. A stenotic aortic valve is narrowed, restricting blood flow from the heart and increasing the potential for heart failure. TAVR is a minimally invasive approach to implanting an artificial heart valve inside a stenotic aortic valve.

During the TAVR procedure, a cardiologist inserts a tube (catheter) through an artery in the groin (transfemoral approach) or a small incision between the ribs (transapical approach). An artificial valve is compressed and fed through the catheter until it reaches the aortic valve. A balloon expands the artificial valve within the patient's stenotic aortic valve, essentially crushing the existing valve, and the catheter is removed. The new valve replaces the old, increasing blood flow throughout the body. A TAVR procedure developed by Edwards Lifesciences PVT, Inc. is described in U.S. Pat. No. 8,002,825 (Implantable Prosthetic Valve for Treating Aortic Stenosis), which is incorporated herein by reference.

Proper alignment of the artificial valve within the stenotic aortic valve is critical to the success of the TAVR procedure. The artificial valve should be positioned as exactly as possible on the crushed stenosed valve, parallel with the aortic annulus. Further, correct alignment of the imaging machines used by the cardiologist in relation to the patient's heart valve is critical to achieving the proper alignment of the artificial valve itself. Traditionally, a cardiologist may use high resolution fluoroscopy and/or cineradiography to view the aortic valve. In such imaging, dye is injected into the aorta, causing the valve to be perceived as a somewhat fuzzy white line on the imaging screen. The cardiologist then attempts to position the imaging machine perpendicular to the valve. Because of the innate imprecision of this method, the cardiologist may need to perform multiple x-ray shots (involving the same number of dye injections). This lengthens the duration of the procedure and increases the risk of complications to the patient.

The TAVR ventricular catheter of the present disclosure aids in the positioning of the C-arm of the imaging machines during a transfemoral TAVR procedure. The catheter is comprised of a hollow resilient tube through which a stiff wire releasably extends. When the wire is extended through the catheter, the catheter conforms to the shape of the wire such that it may be passed through the aortic artery. Once through the artery, the catheter may be deployed by removing the wire, at which point the distal end of the catheter becomes generally circular or oval ring that is positionable adjacent to and snugly beneath the existing stenotic valve. The distal circle can then be used to position the x-ray C-arm in position perpendicular to the aortic valve annulus. The proper C-arm angle is obtained when the distal horizontal circle no longer appears as a circle or ellipse, but as a straight line. This line also identifies the location for optimal valve positioning before valve deployment. The cine picture of this can be stored on a second monitor screen for reference during the actual valve positioning.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

The disclosure can be better understood with reference to the following drawings. The elements of the drawings are not necessarily to scale, emphasis instead being placed upon clearly illustrating the principles of the disclosure. Furthermore, like reference numerals designate corresponding parts throughout the several views.

FIG. 1 is a front perspective view of an embodiment of a TAVR ventricular catheter in accordance with the present disclosure.

FIG. 2 is a top plan view of the exemplary catheter illustrated in FIG. 1.

FIG. 3 is a right side plan view of the exemplary catheter illustrated in FIG. 1.

DETAILED DESCRIPTION

Figure 4:
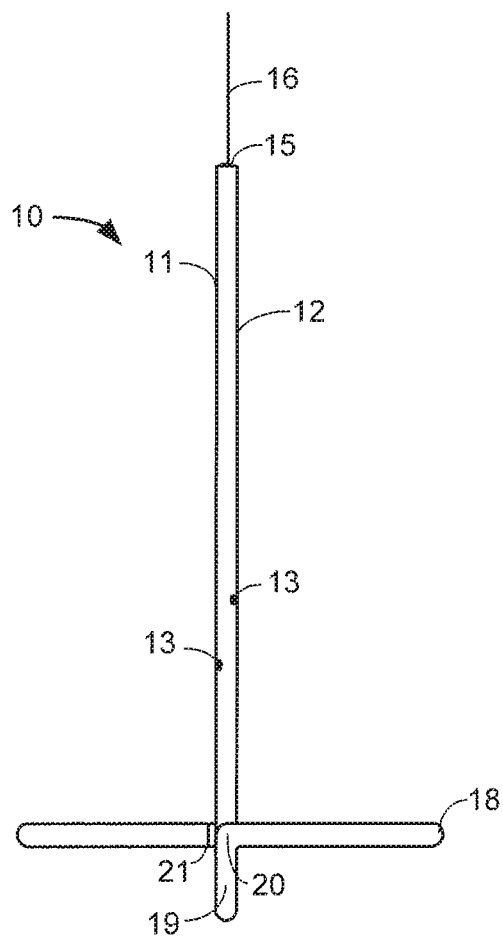
FIG. 4 is a front plan view of the exemplary catheter illustrated in FIG. 1.
Figure 5:
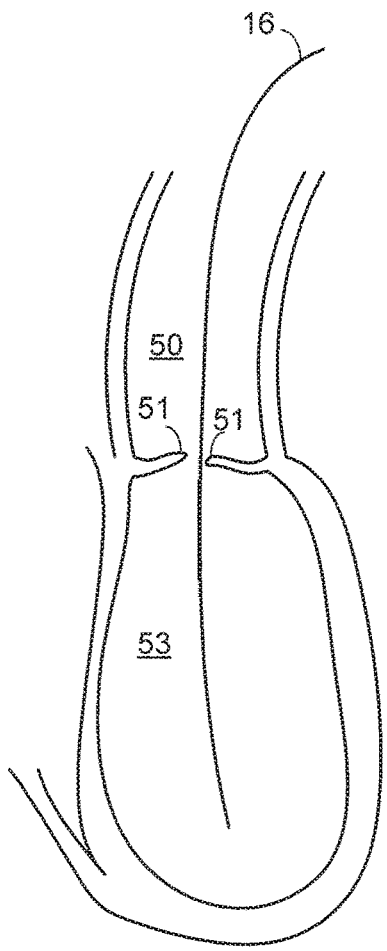
FIG. 5 depicts a guide wire entering the left ventricle, in accordance with an exemplary embodiment of a method for using the catheter of FIG. 1.
Figure 6:
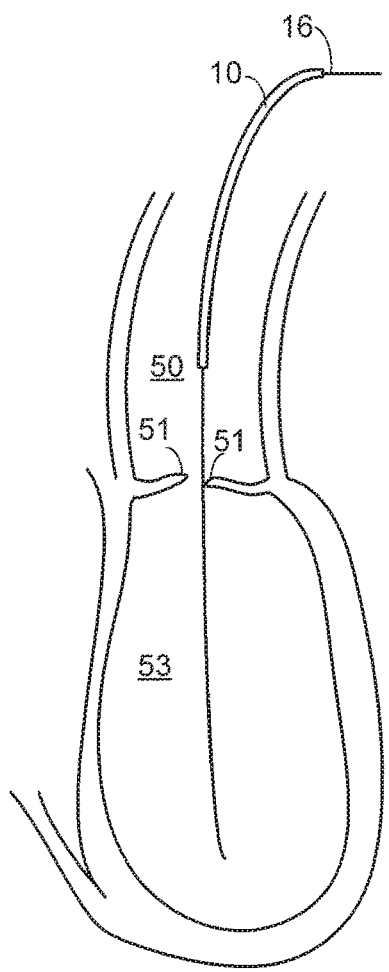
FIG. 6 depicts the catheter being guided into a patient's aorta along the guide wire of FIG. 5.

FIG. 1 is a front perspective view of a TAVR ventricular catheter 10 according to an exemplary embodiment of the present disclosure, with the catheter 10 in its deployed configuration. In this regard, when the catheter 10 is inserted into an aorta (not shown), a guide wire 16 extends completely through the catheter 10. The guide wire 16 is stiffer than the catheter 10, and the catheter 10 is soft and flexible such that the catheter 10 conforms to the shape of the guide wire 16 when the guide wire 16 is extended through the catheter 10. The guide wire 16 is partially withdrawn from the catheter 10 to deploy the catheter 10, which then forms the deployed shape shown in FIG. 1.

The catheter 10 comprises a hollow cylindrical body 11 with an upper opening 15 and a lower opening 14. The catheter 10 is formed in one piece from a flexible material that is soft enough to conform to the guide wire 16. In one embodiment, the catheter 10 is formed via thin wall extrusion. The openings 15 and 14 receive the guide wire 16, which is insertable through the upper opening 15, passes though the catheter 10, and passes through the lower opening 14. When the guide wire 16 is retracted, an upper shaft portion 12 is generally straight and extends downwardly from the upper opening 15 to an outward curve 33 (FIG. 3), at which outward curve 33 the catheter 10 curves downwardly and outwardly. An upward curve 34 (FIG. 3) adjacent to the outward curve 33 extends upwardly and outwardly to form a lower loop 19 (FIG. 3). A distal ring 18 extends circularly generally perpendicularly to the upper shaft portion 12 and joins the lower loop 19 at bend 20.

The lower opening 14 is disposed at a lower end 21 of the catheter 10. A plurality of openings 13 extend through a wall of the catheter 10 and allow the introduction of contrast medium (not shown) used to capture an image of the artery (not shown).

FIG. 2 is a top plan view of the catheter 10 of FIG. 1. The distal ring 18 extends from the bend 20 generally circularly or ovally and terminates at the lower end 21 of the catheter 10. The diameter of the distal ring 18 approximates the diameter of the patient's aortic annular ring (not shown) on the ventricular side, which is generally in the range of 20 to 30 mm. The lower end 21 terminates close to, but does not touch, the bend 20. The lower loop 19 extends from the upper shaft portion 12 to the distal ring 18 via the outward curve 33 (FIG. 3), the upward curve 34 (FIG. 3) and the bend 20. When viewed from the top as shown, the lower loop 19 appears as a substantially straight line between the upper shaft portion 12 and the distal ring 18.

The upper shaft portion 12 of the catheter 10 is centrally disposed within the distal ring 18 in the illustrated embodiment, when the catheter 10 is viewed from the top. This configuration allows the upper shaft portion 12 to extend through the aortic valve (not shown) when the catheter 10 is deployed, while the distal ring 18 is beneath the leaflets (not shown) of the aortic valve, as discussed further with respect to FIG. 9 herein. In other words, because the opening in the aortic valve is located generally in the center of the valve, the upper shaft portion 12 is located generally in the center of the distal ring 18.

FIG. 3 is a side plan view of the catheter 10 of FIG. 1. The distal ring 18 is generally perpendicular to the upper shaft 12 in this embodiment. Importantly, an outer surface of the distal ring 18 is radiopaque, i.e., is discernible under x-ray fluoroscopy.

The lower loop 19 is comprised of the outward curve 33, which curves downwardly and outwardly from the upper shaft portion 12, and the upward curve 34, which curves upwardly and outwardly from the outward curve 33. The bend 20 connects the upward curve 34 to the distal ring 18. The lower loop 19 extends below a plane containing distal ring 18. In one embodiment, the lower loop 19 is generally semi-circular in shape.

Other embodiments of the catheter 10 do not include a lower loop 19, and instead, the upper shaft portion 12 bends generally 90 degrees in the plane of the distal loop 18 and a straight section of tubing (in the same plane as the distal loop 18) joins the distal loop 18 to the upper shaft portion 12. In such an embodiment, the catheter 10 appears as in inverted letter "T" when viewed from the side.

FIG. 4 is a front plan view of the catheter 10 of FIG. 1. As discussed above, the lower end 21 terminates close to the bend 20. The bend 20 transitions the lower loop 19 to the distal ring 18.

In the TAVR procedure that is known in the art (which is described generally in U.S. Pat. No. 8,002,825), an entry wire is first introduced into a puncture in the femoral artery and advanced through the aorta. A conventional guide catheter (not shown) that is known in the art (e.g., Amplatz left ventricle catheter) is advanced along the entry wire and is used to cross the aortic valve and into the left ventricle cavity. The guide wire is retracted and replaced with a stiffer wire, which is subsequently used as the guiding wire for the balloon that will be used to open and "crush" the stenotic aortic valve, before the replacement valve is installed. The conventional guide catheter is then withdrawn.

At this point, the procedure to install the catheter 10 according to the present disclosure begins, as is illustrated in FIGS. 5-9. Referring to FIG. 5, the guide wire 16 is advanced through the patient's aorta 50 and across the aortic valve annulus 51 and into the left ventricle cavity 53. [Note that the balloon guide wire discussed above is not shown in FIGS. 5-9, as it is not related to the procedure for installing and using the catheter 10.] As shown in FIG. 6, the catheter 10 is then advanced along the guide wire 16 into the patient's aorta. The catheter 10 conforms to the shape of the guide wire 16.

Figure 7:
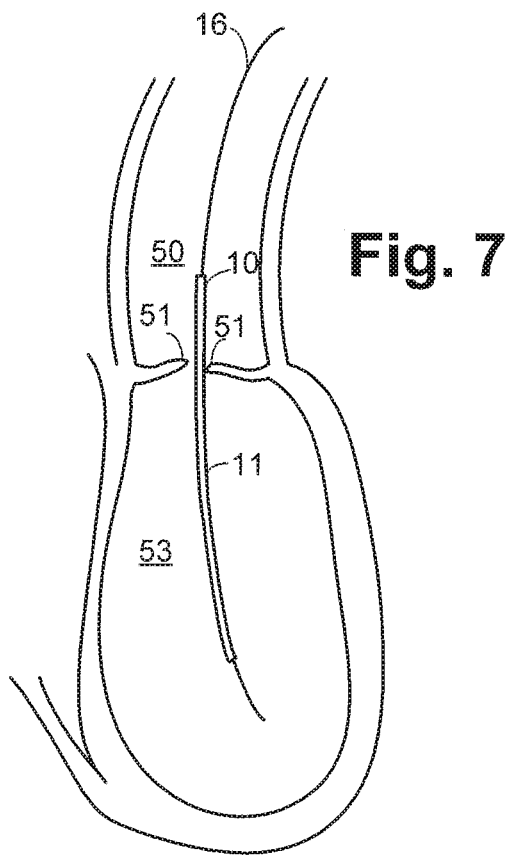
FIG. 7 depicts the catheter being guided into a patient's left ventricle along the guide wire of FIG. 5
Figure 8:
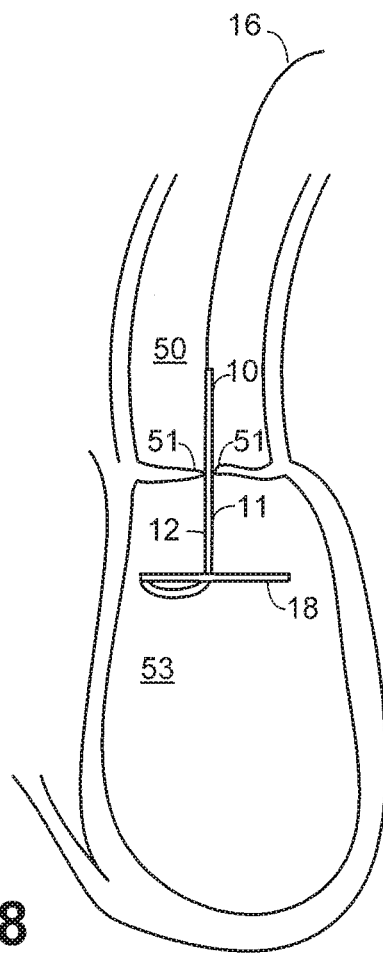
FIG. 8 depicts the catheter of FIG. 1 being deployed in the patient's left ventricle.
Figure 9:
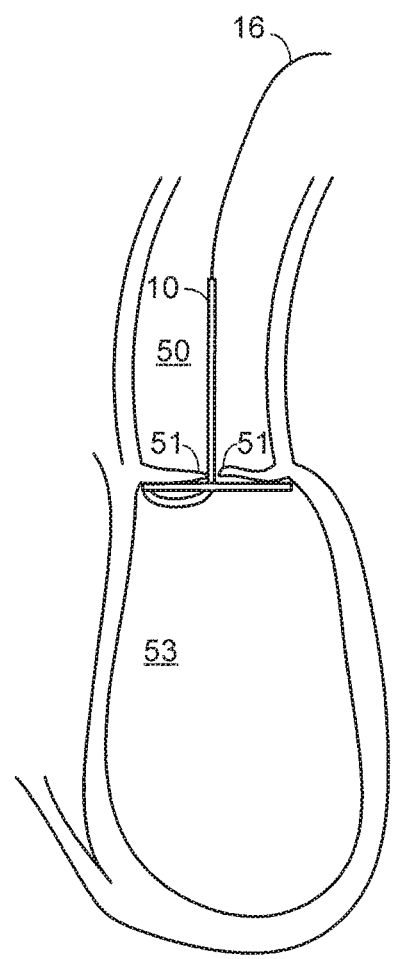
FIG. 9 depicts the catheter of FIG. 1 being retracted snug against the patient's aortic valve annulus.

FIG. 7 depicts the catheter 10 being advanced along the guide wire 16 until the catheter 10 passes through the aortic valve annulus 51, such that most of the hollow cylindrical body 11 has passed through the aortic valve annulus 51 and into the left ventricle cavity 53. The guide wire 16 is then withdrawn from the catheter 10 such that the body 11 of the catheter 10 can resume its deployed state in the left ventricle, as illustrated in FIG. 8. The cardiologist then retracts the catheter 10 until the distal ring 18 contacts and is snugly against the aortic valve annulus 51, as shown in FIG. 9.

Radio opaque fluid (not shown) may be injected through the catheter 10 to perfuse through the openings 13 (FIG. 1) into the left ventricle cavity 53. The cardiologist may then observe by fluoroscopy that the radiopaque distal ring 18 is snugly contacting the stenosed aortic valve. In this regard, the calcification of a stenosed aortic valve can be seen by fluoroscopy to be directly adjacent to the radiopaque distal ring 18 of the catheter 10.

The radiopaque distal ring 18 can then be used to position the x-ray C-arm (not shown) in position coplanar with the aortic valve annulus 51. The proper C-arm angle is obtained when the radiopaque distal ring 18 no longer appears as a circle or ellipse, but a straight line. This line also identifies the location for optimal positioning of the valve before valve deployment. The cine picture of this can be stored on a monitor screen for reference during the actual valve positioning.

After the C-arm is properly positioned, the cardiologist can then advance the guide wire 16 such that the catheter 10 resumes the shape of the guide wire 16, as shown in FIG. 11.

The invention claimed is:

1. A method of positioning an x-ray C-arm in coplanar alignment with an aortic valve, the method comprising:
   advancing a guide wire into a patient's aorta, across the patients aortic valve annulus, and into the patient's left ventricle cavity;
   advancing an undeployed catheter along the guide wire into the patient's aorta, across the patient's aortic valve annulus, and into the patient's left ventricle cavity;
   retracting the guide wire until the undeployed catheter deploys to form a deployed catheter, the deployed catheter comprising
   a distal ring, the distal ring comprising a radiopaque outer surface and a plurality of openings for dispersing contrast medium; and
   a substantially straight upper shaft connecting to the distal ring via a plurality of curves, the upper shaft disposed substantially perpendicularly to the distal ring, the distal ring, the upper shaft and the plurality of curves all formed unitarily from a resilient hollow tube;

retracting the deployed catheter until the deployed catheter contacts the patient's aortic valve on the ventricular side of the aortic valve and on opposite sides of the aortic valve annulus, the upper shaft extends through the aortic valve and the distal ring is beneath the leaflets of the aortic valve;

injecting radio opaque fluid into the deployed catheter to confirm catheter position; and positioning the C-arm using images of the distal ring.

2. The method of claim 1, wherein the plurality of curves comprises an outward curve at which the hollow tube curves outwardly from the upper shaft portion.

3. The method of claim 2, wherein the plurality of curves further comprises a lower loop formed by the outward curve and an upward curve of the hollow tube adjacent to the outward curve.

4. The method of claim 3, wherein the plurality of curves further comprises a bend connecting the upward curve of the hollow tube to the distal ring.

5. The method of claim 4, wherein the lower loop extends below a plane of the distal ring.

6. A method of imaging an aortic valve, the method comprising:

advancing a guide wire into a patient's aorta, across the patient's aortic valve annulus, and into the patient's left ventricle cavity;

advancing an undeployed catheter along the guide wire into the patient's aorta, across the patient's aortic valve annulus, and into the patient's left ventricle cavity;

retracting the guide wire until the undeployed catheter deploys to form a deployed catheter, the deployed catheter comprising a distal ring, the distal ring comprising a radiopaque outer surface and a plurality of openings for dispersing contrast medium; and an upper shaft connecting to the distal ring via a plurality of curves, the distal ring, the upper shaft and the plurality of curves all formed unitarily from a resilient hollow tube;

retracting the deployed catheter until the deployed catheter contacts the patient's aortic valve on the ventricular side of the aortic valve and on opposite sides of the aortic valve annulus, the upper shaft extends through the aortic valve and the distal ring is beneath the leaflets of the aortic valve;

injecting radio opaque fluid into the deployed catheter; and obtaining images of the distal ring.

7. The method of claim 6, further comprising positioning imaging equipment using the images of the distal ring.

8. The method of claim 7, wherein the imaging equipment comprises an x-ray C-arm.

9. The method of claim 8, wherein the step of positioning imaging equipment using the images of the distal ring further comprises positioning the x-ray C-arm in coplanar alignment with the aortic valve.

10. The method of claim 6, wherein the plurality of curves comprises an outward curve at which the hollow tube curves outwardly from the upper shaft portion.

11. The method of claim 6, wherein the upper shaft is substantially straight.

12. The method of claim 11, wherein the upper shaft is disposed substantially perpendicularly to the distal ring.

13. The method of claim 11, wherein the plurality of curves further comprises a lower loop formed by the outward curve and an upward curve of the hollow tube adjacent to the outward curve.

14. The method of claim 13, wherein the plurality of curves further comprises a bend connecting the upward curve of the hollow tube to the distal ring.

15. The method of claim 14, wherein the lower loop extends below a plane of the distal ring.

* * * * *